(12) United States Patent
Vitello et al.

(10) Patent No.: US 7,442,180 B2
(45) Date of Patent: Oct. 28, 2008

(54) APPARATUS AND METHODS FOR ADMINISTERING BIOACTIVE COMPOSITIONS

(75) Inventors: Christopher John Vitello, Corvallis, OR (US); William F. King, Eagle, ID (US); Eric L. Ames, Boise, ID (US); Frederic Adam Ornellas, Boise, ID (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 685 days.

(21) Appl. No.: 10/459,065

(22) Filed: Jun. 10, 2003

(65) Prior Publication Data

US 2004/0254527 A1     Dec. 16, 2004

(51) Int. Cl.
A61M 31/00 (2006.01)
(52) U.S. Cl. .................................................. 604/65
(58) Field of Classification Search .......... 604/253, 604/173, 82, 85, 70, 81, 80, 890.1, 65, 191; 417/179; 705/2
See application file for complete search history.

(56) References Cited

U.S. PATENT DOCUMENTS

| | | | |
|---|---|---|---|
| 3,737,251 A | 6/1973 | Berman et al. | |
| 3,874,826 A | 4/1975 | Lundquist et al. | |
| 3,985,133 A | 10/1976 | Jenkins et al. | |
| 4,335,835 A | 6/1982 | Beigler et al. | |
| 4,557,725 A | 12/1985 | Heyne et al. | |
| 4,583,975 A * | 4/1986 | Pekkarinen et al. | 604/253 |
| 4,683,481 A | 7/1987 | Johnson | |
| 4,786,803 A | 11/1988 | Majette et al. | |
| 4,795,429 A * | 1/1989 | Feldstein | 604/80 |
| 4,835,435 A | 5/1989 | Yeung et al. | |
| 4,857,048 A * | 8/1989 | Simons et al. | 604/503 |
| 4,872,028 A | 10/1989 | Lloyd | |
| 4,915,688 A * | 4/1990 | Bischof et al. | 604/83 |
| 4,922,268 A | 5/1990 | Osborne | |
| 4,990,932 A | 2/1991 | Houston | |
| 4,992,808 A | 2/1991 | Bartky et al. | |
| 5,278,584 A | 1/1994 | Keefe et al. | |
| 5,419,684 A | 5/1995 | Struble et al. | |
| 5,420,627 A | 5/1995 | Keefe et al. | |
| 5,512,046 A | 4/1996 | Pusinelli et al. | |
| 5,873,731 A * | 2/1999 | Prendergast | 434/262 |
| 5,881,716 A * | 3/1999 | Wirch et al. | 128/200.16 |
| 5,894,841 A | 4/1999 | Voges | |
| 6,102,897 A * | 8/2000 | Lang | 604/246 |

(Continued)

FOREIGN PATENT DOCUMENTS

EP            0824022       * 12/1996

(Continued)

*Primary Examiner*—Nicholas D. Lucchesi
*Assistant Examiner*—Christopher D Koharski

(57) ABSTRACT

Bioactive agents are dosed by a jet dispenser using inkjet technology, such as that used in printing devices. The jet dispenser dispenses precise amounts of bioactive agent into a fluid manifold, in which the bioactive agent can be mixed with an infusion liquid for infusing into a patient. A controller may control delivery of one or more drugs, timing of drug administration, or change drug regimens in response to a changing medical condition of a patient. A drop detector can be used to detect various characteristics of the droplets of the bioactive agent dispensed by the jet dispenser and provide a feedback signal to the controller to determine whether a detected characteristic satisfies a predetermined condition. Methods for administering bioactive agents using a jet dispenser also are disclosed.

20 Claims, 8 Drawing Sheets

U.S. PATENT DOCUMENTS

| | | |
|---|---|---|
| 6,123,861 A | 9/2000 | Santini, Jr. et al. |
| 6,149,968 A | 11/2000 | Shimada |
| 6,186,619 B1 | 2/2001 | Usui et al. |
| 6,193,343 B1 | 2/2001 | Norigoe et al. |
| 6,270,478 B1 | 8/2001 | Mernøe |
| 6,474,786 B2 | 11/2002 | Percin et al. |
| 6,491,666 B1 * | 12/2002 | Santini et al. ............... 604/191 |
| 6,530,640 B1 | 3/2003 | Vega et al. |
| 2003/0065294 A1 | 4/2003 | Pickup et al. |

FOREIGN PATENT DOCUMENTS

| | | |
|---|---|---|
| EP | 0 824 022 | 2/1998 |
| EP | 0 985 420 | 3/2000 |
| EP | 1 306 219 | 5/2003 |
| WO | WO 00/16981 | 3/2000 |

* cited by examiner

APPARATUS AND METHODS FOR ADMINISTERING BIOACTIVE COMPOSITIONS

FIELD

This invention relates to administration of compositions (such as pharmaceutical compositions), including compositions administered via infusion. In particular, this invention combines the unrelated technologies of pharmaceutical administration and inkjet technology.

BACKGROUND

In hospitals and other medical facilities, it is often necessary to administer medication to a patient by infusing the medication into the patient through a catheter that is connected to the circulatory system of the patient, for example by infusion into a blood vessel. A common infusion technique involves introducing into the patient a solution containing a medication and an infusion liquid, which serves as a diluent for the medication. In some instances, the medication can be supplied directly to the patient without an infusion liquid. An infusion can involve dispensing the fluid to the subject by gravity or actively pumping the fluid into the subject using a device known as an infusion pump.

Unfortunately, current systems for administering drugs by way of infusion suffer from several disadvantages. For example, the mechanical components of infusion pumps are prone to wear, which can make it difficult to accurately control the volumetric amount of fluid supplied to the subject.

Devices and methods are disclosed herein for improving the administration of infused drugs, by using inkjet-type droplet dispensers that are conventionally used for dispensing ink in a printing mechanism.

SUMMARY

The present disclosure concerns embodiments of an apparatus and method for accurately dosing a bioactive composition in infusions. In one embodiment, a dispensing apparatus for dosing a bioactive composition includes multiple jet dispensers. The dispensing apparatus also includes a mixing unit having a plurality of mixing chambers. Each jet dispenser is operable to dispense a controlled amount of a bioactive composition into a respective mixing chamber. Each mixing chamber has an inlet for receiving an infusion liquid for mixing with the bioactive composition and an outlet for discharging a mixture of the infusion liquid and the bioactive composition, which is then delivered to a subject.

DETAILED DESCRIPTION

Figure 1:
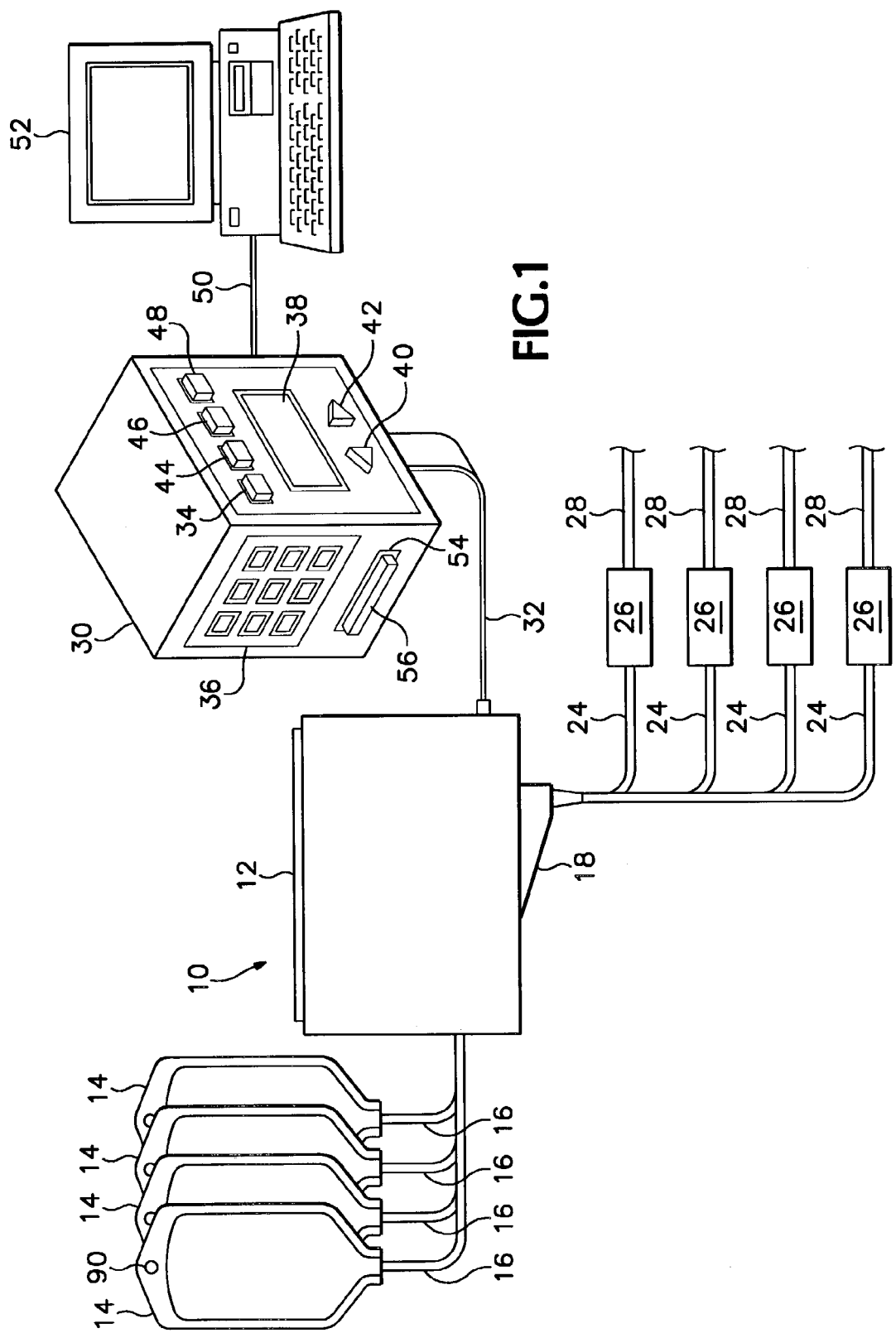
FIG. 1 is an overall schematic view of one embodiment of an infusion system for simultaneously administering multiple medications to a subject.

Unless otherwise noted, technical terms are used according to conventional usage. Definitions of common terms in pharmacology may be found in *Remington: The Science and Practice of Pharmacy*, $19^{th}$ Edition, published by Mack Publishing Company, 1995 (ISBN 0-912734-04-3).

The singular forms "a," "an," and "the" refer to one or more than one, unless the context clearly dictates otherwise.

As used herein, the term "comprises" means "includes."

As used herein, a group of individual members stated in the alternative includes embodiments relating to a single member of the group or combinations of multiple members. For example, the term "antibiotic, bronchodilator, or vitamin," includes embodiments relating to "antibiotic," "bronchodilator," "vitamin," "antibiotic and bronchodilator," "bronchodilator and vitamin," "antibiotic and vitamin," and "antibiotic, bronchodilator, and vitamin."

A "bioactive" composition, substance, or agent is a composition that affects a biological function of a subject to which it is administered. An example of a bioactive composition is a pharmaceutical substance, such as a drug or antibiotic, which is given to a subject to alter a physiological condition of the subject such as a disease. Bioactive substances, compositions, and agents also include other biomolecules, such as proteins and nucleic acids, or liposomes and other carrier vehicles that contain bioactive substances. Bioactive compositions also may include pharmaceutical carriers, adjuvants, and salts.

"Drug" includes any bioactive composition administered for a therapeutic (including diagnostic) purpose.

As used herein, the term "infusion" refers to the introduction of a fluid into a subject, such as the intravascular, intramuscular, intraorbital, subcutaneous, intrahepatic, intralymphatic, or intrathecal introduction of a fluid. The infusion can include flowing or dripping the fluid into the subject by gravity or pumping the fluid into the subject with the aid of a pump. An "infusion liquid" includes any fluid, such as water or a saline solution, that is mixed with a drug and infused into a subject.

As used herein, the term "jet dispenser" refers to a fluid dispenser having a construction similar to an inkjet dispenser used in inkjet printing technology. The construction of the jet dispensers in the disclosed embodiments can be modified from a conventional inkjet construction to accommodate, for example, the characteristics of the particular fluid to be dispensed. In the embodiments disclosed herein, the jet dispenser can be, for example, a piezoelectric inkjet type dispenser or a thermal inkjet type dispenser, which are further discussed below.

The present disclosure concerns embodiments of an apparatus and method for accurately dosing a bioactive composition in infusions. In particular embodiments, a dispensing apparatus for dosing a bioactive composition includes a jet dispenser, such as a thermal jet dispenser or a piezoelectric jet dispenser, having a construction similar to an inkjet dispenser used in inkjet printing technology. The jet dispenser propels precise amounts of the bioactive composition in the form of small droplets into a fluid manifold, in which the droplets mix with an infusion liquid. The fluid manifold has a fluid inlet for receiving the infusion liquid and an outlet for discharging a solution of the infusion liquid and the bioactive composition into a fluid conduit, such as a catheter, for delivery to a subject. The solution may be allowed to flow directly into a subject by gravity. Alternatively, the solution may be fed to a pump for applying a positive pressure to the solution to facilitate infusion of the solution into the subject.

In one representative embodiment, a dispensing apparatus includes a plurality of jet dispensers and a fluid manifold having a plurality of mixing chambers. Each jet dispenser is operable to dispense a controlled amount of a bioactive composition into a respective mixing chamber. Each mixing chamber has an inlet for receiving an infusion liquid to be mixed with the bioactive composition and an outlet for discharging a mixture of the infusion liquid and the bioactive composition. In certain embodiments, the dispensing apparatus has a plurality of fluid reservoirs for containing and delivering the bioactive composition to the jet dispensers. The fluid reservoirs can be separate components, or alternatively, the fluid reservoirs can be a series of individual spaces or compartments formed within an integral fluid reservoir unit.

The dispensing apparatus also may include a controller for manually or automatically dispensing the bioactive substance from the dispenser at selected times and at specified rates. The controller may take the form of an actuator that is manually depressed to activate the dispenser and dispense the agent. Alternatively, the controller may be a programmable device, such as a microprocessor, that is programmed to dispense the bioactive agent at predetermined intervals, for example several times a day. In some embodiments, the controller includes an audible or visible cue, such as a tone or light, to alert the subject that a dose of the bioactive composition is ready to be dispensed. Alternatively, the controller may be used to adjust the dosage of an administered drug for a particular circumstance, such as a particular time of day, an event (such as an activity that will require a dosage modification), or detection of a physiological condition (such as an adverse drug reaction that requires reduction or cessation of drug administration). Complex administration protocols may be followed, for example applying different drugs at different times throughout the day or for longer periods, such as a week, a month, or even longer.

Using existing inkjet technology, exact dosing of the drug may be achieved. Controllers may be used to dispense simple or complex drug regimens, which is of particular advantage in patients who require numerous daily medications. Computerized control of medication dosing, which may be programmed by medical personnel for subsequent automated delivery, can help avoid toxic drug interactions, overdoses, and deaths.

The dispensers disclosed herein may be similar to fluid dispensers known as inkjet printheads used in inkjet printing mechanisms, such as printers, plotters, facsimile machines and the like, some of which are described, for example, in Durbeck and Sherr, *Output Hardcopy Devices*, Academic Press Inc., 1987 (ISBN 0-12-225040-0), particularly in chapter 13, pages 311-370. These technologies have in common the extraction of a small quantity of a fluid from a reservoir that is converted into fine droplets and transported through the air to a target medium by appropriate application of physical forces. This technology has been implemented in a variety of ways, but one of the common approaches has been thermal inkjet technology, in which liquids are heated using resistors to form drops and propel them from a chamber through an orifice toward a target. Another approach is piezoelectric inkjet technology, in which movement of a piezoelectric transducer changes a chamber volume to generate the drop.

A typical jet printing mechanism uses cartridges (often called "pens") which shoot drops of liquid colorant (generally referred to as "ink") onto a page. Each cartridge includes a printhead formed with very small nozzles through which the ink drops are fired. Most often, the printhead is held in a carriage which slides back and forth along a guide rod in a reciprocating printhead system, with a target or print media, such as paper, being advanced in steps between each pass of the printhead. To print an image on media, the printhead is scanned back and forth across the page, shooting drops of ink in a desired pattern as it moves. Other printing systems known as "page-wide array" printers, extend the printhead across the entire page in a stationary location and print as the media advances under the printhead. The particular liquid ejection mechanism within either type of printhead may take on a variety of different forms, such as the piezoelectric or thermal printhead technology.

For example, two thermal ink ejection mechanisms are shown in U.S. Pat. Nos. 5,278,584 and 4,683,481, both assigned to the Hewlett-Packard Company. In a thermal system, a barrier layer containing fluid channels and vaporization chambers is located between a nozzle orifice plate and a substrate layer. The substrate layer typically contains linear arrays of heater elements, such as resistors, which are energized to heat ink within the vaporization chambers. Upon heating, an ink droplet is ejected from a nozzle associated with the energized resistor. By selectively energizing the resistors as the printhead moves across the page, the ink is expelled in a pattern on the print media to form a desired image (e.g., picture, chart, or text).

In piezoelectric inkjet technology, an activating pulse is applied to a piezoelectric plate or member attached to a plate, which then responds by flexing to propel an ink drop out of a nozzle. Several examples of piezo-electric inkjet printheads are described in U.S. Pat. Nos. 4,992,808; 6,186,619; and 6,149,968 (assigned to Xaar Technology Ltd.) and U.S. Pat. No. 6,193,343 and WO 00/16981 (assigned to Seiko Epson Corporation).

In a common cartridge configuration, both the fluid reservoir and the printhead are carried by a carriage along the guide rod of the printer. Such printers are known as an "on-axis" printers. Some on-axis printers use "snapper" reservoir systems, in which permanent or semi-permanent printheads are used in conjunction with a detachable reservoir carrying a fresh liquid supply, with the reservoir being snapped into place on the printhead. Another design uses permanent or semi-permanent printheads in what is known in the industry as an "off-axis" printer. In an off-axis system, the printheads carry only a small liquid supply reciprocally back and forth across the printzone, with this on-board supply being replenished through tubing that delivers liquid from an "off-axis main reservoir" placed at a remote, stationary location within or near the printhead. In both the snapper and off-axis systems, rather than purchasing an entire new cartridge which includes a costly new printhead, the consumer buys only a new supply of liquid for the main reservoir or a replacement reservoir already filled with fluid.

In striving to duplicate the quality of photographic film images, the inkjet industry has focused on decreasing the size of ink droplets ejected from the nozzles, as well as accurately placing these droplets on the print media. For instance, some of the more recent inkjet print cartridges are able to deliver droplets about 3-6 picoliters in volume, although larger droplets also may be generated, for example droplets of 10, 50, 100, or more picoliters. The resolution within which currently commercially available inkjet printing mechanisms may place ink droplets on a page is on the order of 1200-2400 dots per inch (known in the industry as a "dpi" rating). Thus, while striving to achieve photographic print quality, inkjet printing technology has become very adept at accurately metering and dispensing fluids. This ability to dispense very small and accurate amounts of fluids (including liquids and powders) is a part of the application systems illustrated herein.

In particular embodiments, the droplet sizes are about 10 μm or less, such as about 2 μm to about 8 μm. In other embodiments, the droplet sizes are greater than 10 μm, or in some cases greater than 100 μm. The size of the droplets ejected from a jet dispenser depends in part on the size of the orifice through which the droplets are ejected. In this regard, some printheads include multiple orifices of varying sizes. This allows a single printhead to be used to selectively dispense droplets of different sizes.

In particular embodiments, one or more drop detectors are employed to detect a characteristic of the droplets of fluid dispensed from a jet dispenser. For example, a drop detector may determine whether any droplets are being dispensed from a particular jet dispenser. Other droplet characteristics that can be detected by a drop detector include the volume and velocity of the droplets. The drop detector sends this information to a controller, which can be used to activate an alarm, such as an audio and/or visual alarm, if the detected characteristic does not satisfy a predetermined condition or requirement. In one specific implementation, for example, an alarm is activated if a drop detector determines that a jet dispenser is not dispensing any drops. In another implementation, a controller stops a jet dispenser from dispensing fluid if it is determined that the jet dispenser is not operating within specified parameters. For example, a controller can be used to monitor the dispensing rate of a jet dispenser and stop the ejection of fluid from the jet dispenser if the dispensing rate exceeds a specified dispensing rate. If desired, historical data of the detected characteristics can be stored in memory of a local controller or a remote computing device. Such data can be used to monitor the past performance of the jet dispensers to determine whether maintenance the apparatus is required, such as cleaning, repairing, or replacing components.

The drops detectors used in the embodiments disclosed herein can be any of various drop detectors known in the art. One type of drop detector is an electrostatic drop detector that charges a drop when the drop is formed. An electrostatic drop detector senses the electric field of the charged drop and produces an output signal in response to the detected drop. An electrostatic drop detector can be used to detect the volume of an ejected drop based upon the amount of electrical charge transferred to an electrostatic sensing element. A similar type of drop detector uses an electrode that, when impacted by a drop, produces a small current to indicate the presence of the drop. Another type of drop detector directs a beam of light at a light sensor (e.g., a photodetector). When a drop passes through the light beam, the output of the light sensor varies accordingly to indicate the detection of the drop. Yet another type of drop detector detects drops that impact a piezoelectric membrane. One such drop detector is disclosed in U.S. Pat. No. 4,835,435 to Yeung et al. U.S. Pat. No. 4,583,975 to Pekkarinen et al., discloses a piezoelectric drop detector mounted to the wall of a chamber. Instead of striking the piezoelectric film directly, the drops strike the surface of accumulated liquid in the chamber and pressure waves travel through the walls of the chamber to the piezoelectric film.

In another representative embodiment, an apparatus for administering a bioactive composition to a subject includes a jet dispenser for dispensing a controlled amount of the bioactive composition in the form of droplets. A fluid manifold is configured to receive the droplets of the bioactive composition dispensed from the jet dispenser. A drop detector detects a characteristic of the droplets dispensed from the jet dispenser. The drop detector can be operatively connected to a controller in a feedback system to provide a warning, such as an audible or visual warning, or to stop the ejection of droplets from a jet dispenser should the drop detector detect a characteristic that does not satisfy a predetermined condition.

In still another representative embodiment, an apparatus for administering a bioactive composition to a subject includes a jet dispenser operable to dispense droplets of the bioactive composition into a fluid chamber. The fluid chamber desirably has a drip surface, a first inlet for receiving an infusion liquid such that the infusion liquid is directed onto the drip surface, a second inlet for receiving the droplets of bioactive composition dispensed from the jet dispenser such that the droplets also are directed onto the drip surface, and a fluid outlet for discharging a mixture of the infusion liquid and the bioactive composition.

In yet another representative embodiment, an apparatus for administering a bioactive composition to a subject includes a plurality of fluid dispensers for dispensing a controlled amount of the bioactive composition and a plurality of fluid chambers for containing and delivering the bioactive composition to the fluid dispensers. The apparatus also includes a fluid manifold having a first inlet for receiving the bioactive composition dispensed from the fluid dispensers, a second inlet for receiving an infusion liquid for mixing with the bioactive composition, and an outlet for discharging a mixture of the infusion liquid and the bioactive composition.

In another representative embodiment, a method for administering a bioactive composition to a subject includes dispensing droplets of the bioactive composition from a plurality of jet dispensers into respective mixing chambers. An infusion liquid is mixed with the bioactive composition in each mixing chamber and a mixture of the infusion liquid and the bioactive composition is discharged from each mixing chamber and infused into a subject. The bioactive composition to be dispensed from each jet dispenser can be the same or different from each other. For example, in one implementation, different bioactive compositions are simultaneously dispensed from the jet dispensers for infusing into the subject.

In another representative embodiment, a method for administering a bioactive composition to a subject includes dispensing from a jet dispenser droplets of the bioactive composition, detecting a characteristic of the droplets dispensed from the jet dispenser, and delivering the bioactive composition to the subject.

More specifically, and referring to FIG. 1, there is shown an infusion system 10, according to one embodiment, for accurately dosing one or more bioactive compositions in infusions. The illustrated system 10 generally includes a dispensing apparatus 12 fluidly connected to one or more fluid containers 14 containing an infusion liquid. The fluid containers 14 can be, for example, flexible bladders, such as plastic bags similar to or identical to the containers which are used to administer intravenous ("IV") fluids to patients in hospitals, ambulances, nursing homes, and the like. The illustrated containers 14 desirably include fixtures, such as eyelets 90, which can be used to hang the containers from a conventional IV stand. In the illustrated system, infusion liquid from the containers 14 is gravity fed into individual fluid chambers (e.g., fluid chambers 22 in FIG. 3) of a fluid manifold 18 (also referred to herein as a mixing unit) via fluid conduits 16, which can be conventional IV tubing. In other embodiments, a single fluid container 14 can be used to supply an infusion liquid to each fluid chamber of the fluid manifold 18.

The dispensing apparatus 12 has multiple fluid reservoirs (e.g., fluid reservoirs 20 in FIG. 3) for containing one or more bioactive compositions, and one or more fluid dispensers (described below) for dosing controlled amounts of bioactive composition from the fluid reservoirs 20 into one or more fluid chambers (also referred to herein as mixing chambers) of the fluid manifold 18. Mixtures of the infusion liquid and the bioactive composition are discharged through fluid conduits 24 that are fluidly connected to the mixing chambers 22. In the illustrated embodiment, the conduits 24 feed the mixtures of the infusion liquid and the bioactive composition to individual pumping units 26. Each pumping unit 26 provides a pressurized flow of fluid to a subject via a respective fluid conduit 28. The pumping units 26 can be conventional infusion pumps. In an alternative implementation, the fluid mixtures can be gravity fed to the subject without the use of the pumping units 26.

As shown in FIG. 1, the system 10 includes a controller 30 for controlling the operation of the dispensing apparatus 12. The controller 30 may be a separate unit electrically connected to the controller 30 with a flexible connector 32, such as shown in FIG. 1. Desirably, the controller 30 is adapted to be mounted or supported by the dispensing apparatus 12. In alternative embodiments, the controller 30 can be integral with the dispensing apparatus 12. The controller 30 and dispensing apparatus 12 receive power either from an onboard battery storage system, which may be located in either the controller 30, the dispensing apparatus 12, or both. Alternatively, power may be supplied from an external source, such a standard electrical outlet. Of course, rechargeable or replaceable batteries may be preferred in some embodiments for ease of portability and use. The controller 30 operates to apply firing signals to the fluid dispensers of the dispensing apparatus 12, which respond by ejecting droplets of fluid from the fluid reservoirs 20 into the fluid chambers 22.

In a simple embodiment, the controller 30 may include an ON/OFF power switch, or button, 34, to which controller 30 responds by beginning and/or ending a fluid ejection sequence. Alternatively, switch 34 may simply serve as an ON switch, with controller 30 determining the precise amount of fluid to be ejected from the fluid dispensers, and then stopping ejection automatically after the selected metered amount has been dispensed. In a more sophisticated embodiment, controller 30 may include an input keypad 36, which can be an alpha or alpha numeric keypad. Using keypad 36, a physician, nurse, pharmacist or other health professional, or the subject to which the fluid will be administered, may input variations in the amount of and types of fluids dispensed. Controller also may include a display screen 38, which can be a liquid crystal display, to indicate which selections have been made using keypad 36 and/or to display different operating parameters of dispensing apparatus 12. Alternatively, keypad 36 may be eliminated, and the controller 30 programmed to display various selections on screen 38. Scrolling buttons 40 and 42 may allow different instructions or selections to be scrolled across, or up and down along, screen 38, including information such as desired dosages, frequency, and potential side effects.

In still other alternative embodiments, the display screen 38 also is a touch screen, in addition to, or in place of, keypad 36. The touch screen may include a series of images that, when touched with a finger or stylus, program the controller 30. Alternatively, the touch screen may include a character recognition area for receiving written inputs using a stylus, such as the graffiti recognition features of the Palm® operating system (Palm, Inc., Santa Clara, Calif.). Thus, a touch screen provides an alternative means for programming the controller in addition to the keypad.

Display screen 38 also may indicate various selections along an upper portion of the screen, adjacent buttons 34, 44, 46 and/or 48, allowing a user to then select a particular drug or dosage by depressing one or more of these buttons. Alternatively, depressing one of the buttons could indicate the occurrence of a particular event, such as an adverse medication response that would alter (for example decrease) a subsequent dosage administration, or an event (such as physical exertion) than can signal a need to alter a medication dosage. The controller also may be programmed to prevent unauthorized alteration of dosages, for example an increase in a dosage of a controlled substance above that authorized by the prescribing physician. Alternatively, the controller can permit certain ranges of dosages to be administered, for example various doses of an opioid pain reliever in response to fluctuating pain.

As shown in FIG. 1, a more expedient method of initially programming controller 30, or supplying dosage and other information, may be to use a computer input link 50, selectively attachable to the controller 30, to couple an external computer, microcomputer, or other computing device 52 to controller 30. Other linkage devices may be used to communicate between external computing device 52 and controller 30, such as by using infrared signals, radio waves, modems, direct connections, and the like. For example, a patient can download information stored in the device about self-regulated dosage administrations or symptoms experienced (as indicated for example by which buttons have been depressed on the device, and/or the pattern and frequency of the buttons that are pushed). This information can be transmitted over a modem to a physician's or other health care provider's office, where it can be displayed (in electronic or other form) to a health care professional, and appropriate action can be taken. For example, if symptoms are noted to be increasing in spite of administration of a therapeutic amount of a particular drug, consideration can be given to providing a new drug or reconsidering the diagnosis for which the drug has been administered. As another example, the controller 30 may include a docking connection for use with a docking station connected to a computer at the physician's office. Thus, connecting the applicator to an external computer provides an alternative means for programming the applicator controller, in addition to the keypad and touch screen mentioned above.

The controller 30 also may be linked to communicate with other devices, such as devices for monitoring the physiological status of a subject. For example, the device may be linked to a blood sugar monitor and programmed to release an anti-diabetic drug if the subject's blood sugar level falls outside the normal range. As another example, the device may be linked to a temperature monitor and programmed to release a fever-reducing (antipyretic) drug if the subject's body temperature rises above a certain threshold. The device may be programmed to automatically release a composition, such as in the case where the device is part of a respiratory mask worn by a bed-ridden patient, or may be programmed to signal the user that a dose of a composition should be administered to the user.

Alternatively, as shown in FIG. 1, controller 30 may define an input slot 54 which is sized to receive an input device, such as a flash memory card 56 or other removable memory device, which carries input data for controller 30. This removable memory device may be programmed by the controller 30 or some external device, such as a remote computer. For example, the removable memory may be inserted into and programmed by a computer at a physician's office, hospital, clinic, or other health facility and given to the subject for use with the applicator. Indeed, use of the flash memory card 56 or similar memory device in conjunction with controller 30, may result in the only other input device of controller 30 being switch 34. Thus, programmable removable memory provides yet another alternative means for programming the applicator controller, in addition to the keypad, touch screen, and remote computer connection described above.

In one embodiment, controller 30 may only have an ON switch 34, and be completely preprogrammed via an external computer 52, such as at a doctor's office or pharmacy, prior to giving the device to a patient. In another embodiment, the device may be sold with only an ON switch 34, and with the physician or pharmacy supplying the medication in a kit with a flash memory card 56.

Figure 2:
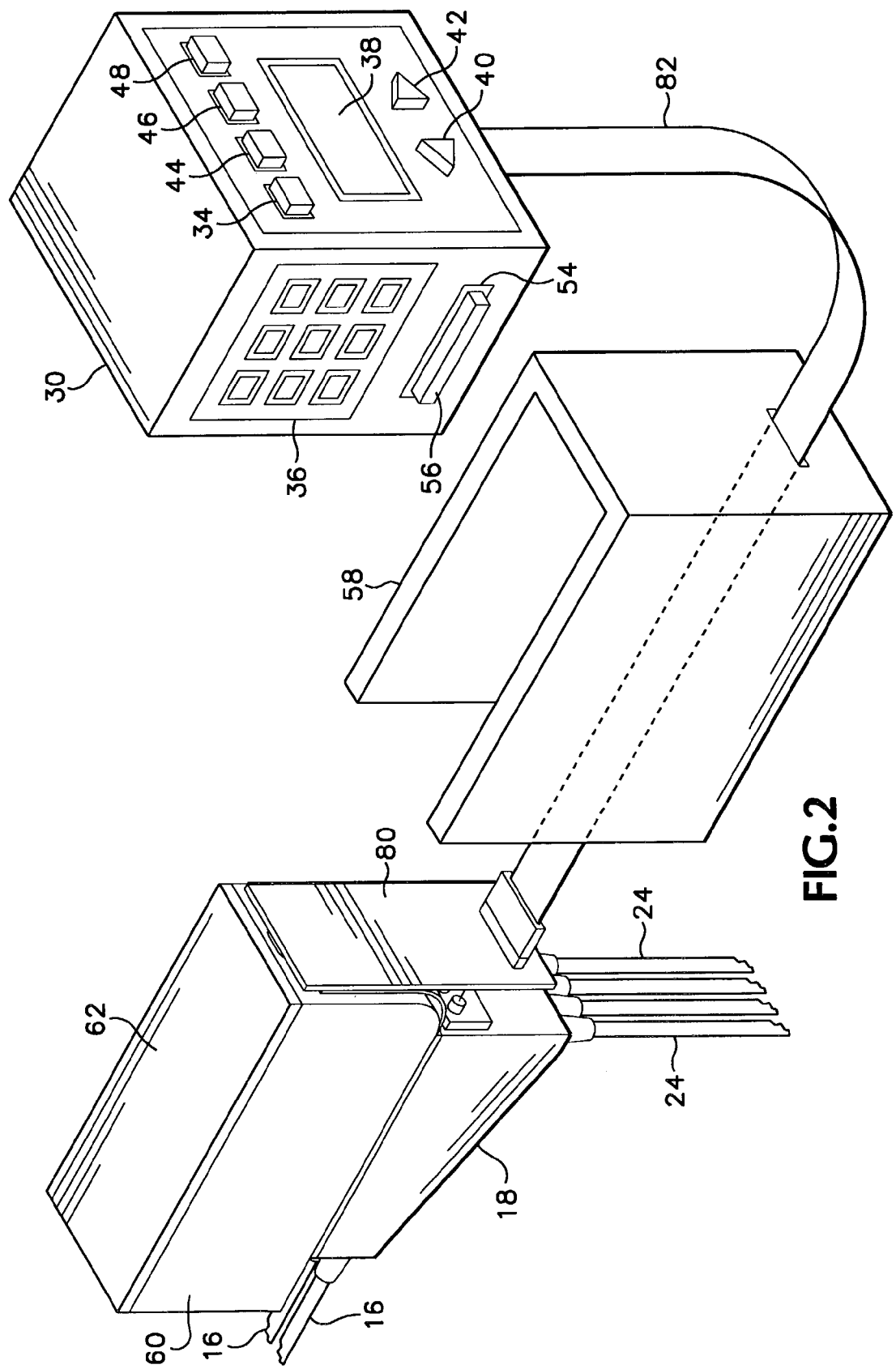
FIG. 2 is a perspective view of a dispensing apparatus, according to one embodiment, for dosing modifications in infusions.
Figure 3:
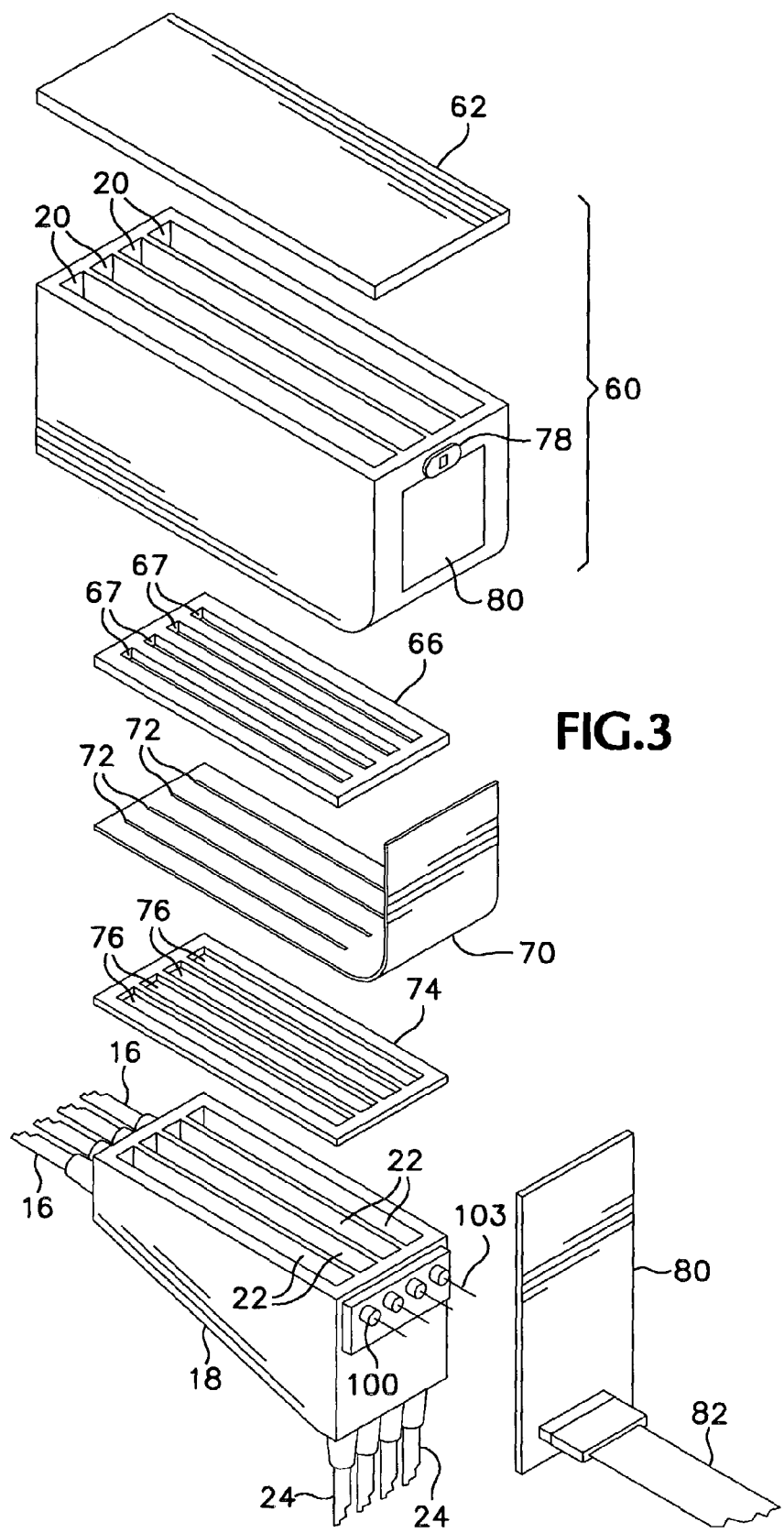
FIG. 3 is a perspective, exploded view of the dispensing apparatus of FIG. 2.
Figure 4:
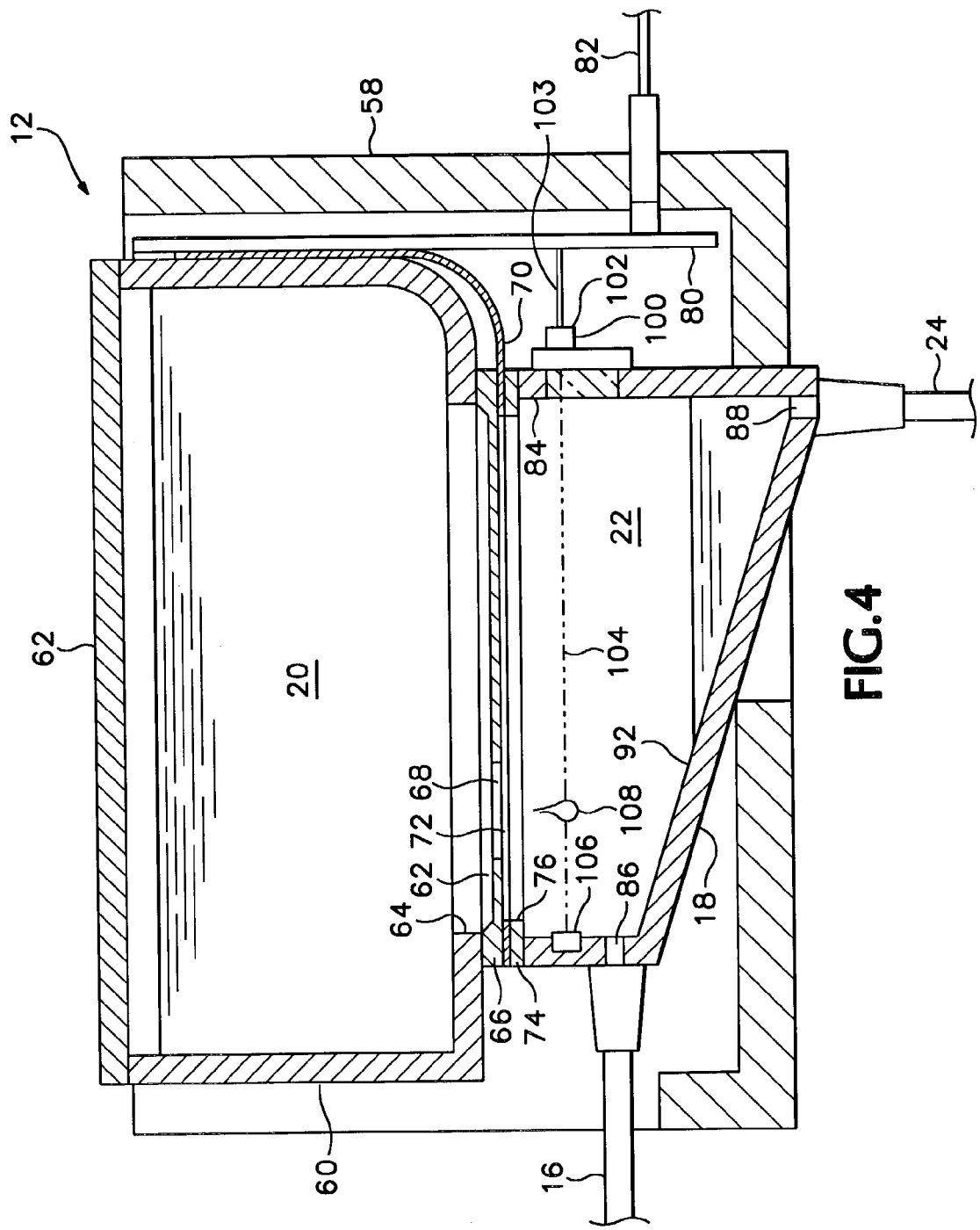
FIG. 4 is a longitudinal cross-sectional view of the dispensing apparatus of FIGS. 2 and 3.

Referring now to FIG. 2-4, the details of one embodiment of a dispensing apparatus 12 will now be described. As shown in FIG. 2, the illustrated dispensing apparatus 12 includes a removable outer housing 58 for housing the fluid manifold 18 and a fluid reservoir unit 60. The fluid reservoir unit 60 defines a plurality of fluid reservoirs 20 (FIG. 3) for containing bioactive compositions. The fluid reservoir unit 60 also has a removable cover, or lid, 62 for accessing the fluid reservoirs 20 inside the unit 60. In alternative embodiments, the fluid reservoirs 20 may serve as receptacles for receiving replaceable and/or disposable fluid reservoirs (not shown) that contain the bioactive compositions. In such an embodiment, the fluid reservoirs may be removed from their respective receptacles when empty and new fluid reservoirs may be inserted into the fluid reservoir unit 60.

The illustrated housing 58 partially covers the fluid manifold 18 and the fluid reservoir unit 60 and serves as a mounting surface for mounting the controller 30. In another embodiment, the housing 58 completely encloses the fluid manifold 18 and the fluid reservoir unit 60, and is formed with apertures or openings for fluid conduits 16 and 24 and a removable cover for accessing the fluid reservoirs 20. In another embodiment, the controller 30 can be integral with the housing 58.

Figure 5A:
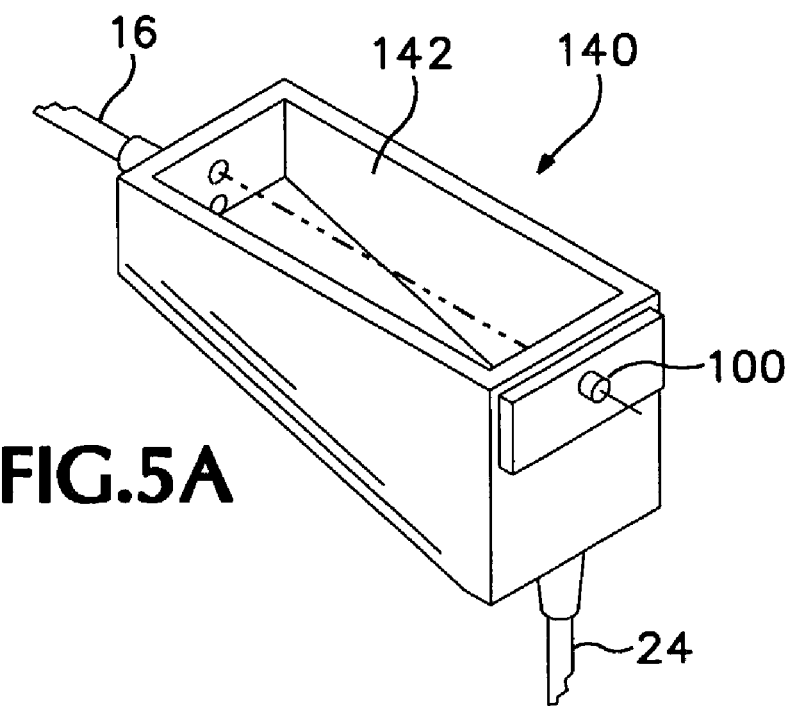
FIG. 5A is a perspective view of an alternative embodiment of a fluid manifold that can be used in the dispensing apparatus of FIGS. 2-4.
Figure 5B:
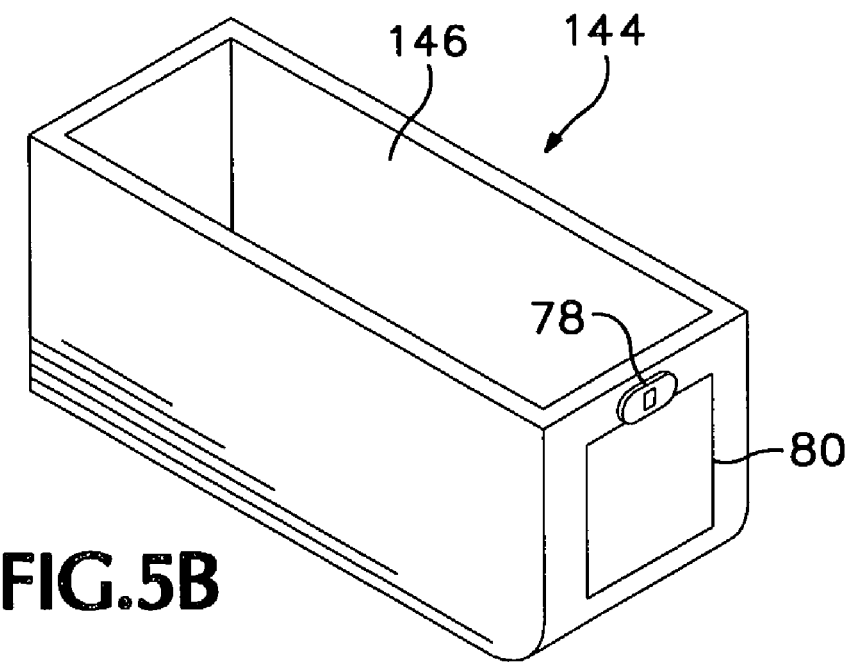
FIG. 5B is a perspective view of an alternative embodiment of a fluid reservoir unit that can be used in the dispensing apparatus of FIGS. 2-4.

As shown in FIG. 4, each fluid reservoir 20 has an outlet opening 64 to allow the bioactive composition to be dispensed into the mixing chambers 22. In the illustrated embodiment, each fluid reservoir 20 is registered with a respective mixing chamber 22 so that fluid from each fluid reservoir 20 will be dispensed into a respective mixing chamber 22. The number of fluid reservoirs 20, however, need not correspond to the number of mixing chambers 22. For example, FIG. 5B shows an alternative embodiment of a fluid reservoir unit 144 that is formed with one fluid reservoir 146 for storing a fluid. The fluid stored in unit 144 can be selectively dispensed into one or more mixing chambers 22 of a fluid manifold 18. In another example, as shown in FIG. 5A, a fluid manifold 140 is formed with one mixing chamber 142, which can be used with fluid reservoir unit 144 or a fluid reservoir unit having multiple fluid reservoirs, such as unit 60.

Interposed between the fluid reservoirs 20 and the mixing chambers 22 are a plurality of fluid dispensers configured to dispense a controlled amount of fluid from the fluid reservoirs 20 into the mixing chambers 22. In particular embodiments, the fluid dispensers are thermal droplet jet dispensers that are operable to heat a volume of fluid to cause the fluid to vaporize and be ejected through an orifice into one of the mixing chambers 22.

As shown in FIG. 3, for example, the illustrated dispensing apparatus 12 includes a substrate 66 (also known as a die) interposed between the reservoir unit 60 and the fluid manifold 18. Substrate 66 is formed with a plurality of generally V-shaped troughs, or channels 67. Each trough 67 is formed with at least one opening, or orifice, 68 (FIG. 4) through which fluid droplets are ejected. The substrate 66 also includes a plurality of individually energizable heater elements (e.g., thin film resistors) (not shown), each being operable to vaporize a volume of fluid, thereby causing the fluid to be ejected through an associated orifice 68, as known in the art. In this manner, each orifice 68 and a respective heater element serves as a thermal jet dispenser for dispensing a controlled amount of fluid. Substrate 66 can be made from any of suitable materials, such as, silicon, glass, or equivalent materials. The construction of substrate 66 can be conventional, such as disclosed in U.S. Pat. No. 5,420,627 to Keefe et al., U.S. Pat. No. 5,278,584 to Keefe et al., or U.S. Pat. No. 4,683,481 to Johnson. In some embodiments, each orifice 68 is of the same size. In other embodiments, the substrate 66 is formed with differently sized orifices 68 for dispensing drops of different sizes.

In the illustrated embodiment, each trough 67 is registered with a respective fluid reservoir 20. In this manner, each fluid reservoir 20 delivers fluid to the orifices 68 of a corresponding trough 67. In alternative embodiments, however, substrate 66 can be configured such that two or more troughs 67 are situated to receive fluid from a single fluid reservoir 20.

A flexible circuit 70 (e.g., a tape automated bond circuit (TAB)) is in electrical contact with conductive traces on the substrate 66 for providing electrical pulses to the heater elements. Circuit 70 can be bonded to the substrate 66 using a suitable adhesive and is formed with a plurality of slots 72 that are aligned with orifices. The construction of circuit 70 can be conventional, such as disclosed in the above-noted patents. A fluid seal 74 having a plurality of openings 76 can be disposed between the circuit 70 and the fluid manifold 18 to prevent, or at least reduce, leakage of fluid and cross-contamination between fluid reservoirs 20. Seal 74 can be made from any suitable materials, such as natural rubber, Teflon®, or various other materials, as known in the art.

In alternative embodiments, other types of jet dispensers can be used. For example, the dispensing apparatus 12 can include a plurality of piezoelectric jet dispensers interposed between the fluid reservoirs 20 and the mixing chambers 22. In other embodiments, fluid dispensers other than jet dispensers can be used for dispensing fluid from the fluid reservoirs 20, although jet dispensers are preferred due to their excellent accuracy and repeatability.

The controller 30 is operatively connected to the heater elements of the substrate 66 to control the firing of fluid from the orifices 68. The illustrated embodiment, for example, includes a printed circuit board 80 mounted to the outside of the fluid reservoir unit 60 and in electrical contact with flexible circuit 70 (FIGS. 2-4). The printed circuit board 80 is electrically connected to the controller 30 via a flexible ribbon connector 82 to complete the electrical connection between the controller and the substrate. Other electrical components can be implemented to permit the controller 30 to control the operation of the jet dispensers via a hardwired connection or a wireless connection.

As best shown in FIG. 4, each mixing chamber 22 has a first fluid inlet 84 aligned with the orifices 68 of a respective trough 67 to receive fluid dispensed therefrom, a second fluid inlet 86 to receive an infusion liquid from a respective fluid conduit 16, and a fluid outlet 88 in communication with a respective fluid conduit 24. As can be appreciated from FIG.

4, droplets of bioactive composition dispensed into a mixing chamber 22 mixes with the infusion liquid in the mixing chamber and a mixture of the infusion liquid and the bioactive composition flow outwardly through outlet 88 into a respective fluid conduit 24.

The manifold 18 desirably, although not necessarily, has a bottom surface 92 that is sloped to direct the accumulated fluid to the outlet 88 (as best shown in FIG. 4). The inlet 86 desirably is positioned at the higher end of the chamber 22 so that the infusion liquid entering the chamber 22 flows over the bottom surface 92 before accumulating at the lower end of the chamber 22. Also, the orifices 68 desirably are positioned such that the ejected droplets 108 impinge the bottom surface 92 before mixing with the accumulated fluid in the chamber 22. In this manner, the bottom surface 92 serves as a "drip" surface for the droplets 108 ejected from orifices 68. By directing the droplets 108 of the bioactive composition onto the bottom surface 92, the incoming infusion liquid flows over the bioactive composition to facilitate dispersion of the bioactive composition in the infusion liquid.

In certain embodiments, the fluid manifold 18 and the fluid reservoir unit 60 are configured to be connectable to and detachable from each other and various fluid manifold and fluid reservoir unit configurations are provided to allow a user to select a specific fluid manifold and fluid reservoir unit configuration for a particular application. For example, when dispensing only one type of bioactive composition, either a reservoir unit having multiple reservoirs (FIG. 3) or a reservoir unit having a single reservoir (FIG. 5B) can be used with a single-chambered fluid manifold (FIG. 5A). In another example, when different bioactive compositions can be mixed together in the same infusion liquid, a single-chambered fluid manifold (FIG. 5A) can be used in lieu of a multi-chambered fluid manifold (FIG. 3).

In one implementation of the dispensing apparatus 12, each fluid reservoir 20 contains a different bioactive composition and the dispensing apparatus 12 is used to simultaneously dose the different bioactive compositions into the mixing chambers 22 at specified dispensing rates. As used herein, the term "dispensing rate" refers to the volumetric flow rate of fluid from a jet dispenser. A user or health care professional can input the prescribed dosage for each bioactive composition into the controller 30, which then controls the firing frequency of each jet dispenser to accurately dose the bioactive compositions into the infusion liquid. In another implementation, each fluid reservoir may carry the same bioactive composition, with the controller 30 dispensing fluid from one fluid reservoir 20 until empty, followed by another fluid reservoir 20, and so forth.

In particular embodiments, the dispensing apparatus 12 has a memory chip, such a programmable memory chip or a flash chip, that contains data relating to certain operating parameters of the jet dispensers. In particular embodiments, for example, the memory of the memory chip contains the average size (i.e., volume) and/or weight of fluid droplets that are dispensed from each orifice 68. In use, a user inputs into the controller 30 the treatment parameters, including the amount of bioactive composition to be administered to the subject, and if desired, the time period over which it is to be administered. The controller 30 is programmed to access this data and calculate the firing frequency required to accurately deliver the prescribed dosage of a bioactive composition to the subject over the specified time period. The controller 30 also can be used in cooperation with one or more drop detectors (e.g., drop detector 100, described below) in a feed-back loop to ensure proper operation of the dispensing apparatus 12, as further described below.

In the illustrated configuration, a memory chip 78 is mounted to the outside of the fluid reservoir unit 60 and is in electrical contact with flexible circuit 70 via another flexible circuit 80. In another embodiment, the memory chip 78 can be physically mounted to a circuit board inside the controller 30. Alternatively, the information stored in the memory chip 78 can be stored directly in the memory of the controller 30 or on flash memory card 56, in which case a separate memory chip would not be required.

To determine whether any jet dispensers are operating in an improper manner, e.g., an orifice 68 is clogged and not dispensing fluid, fluid sensors, such as the illustrated optical drop detectors 100, are positioned below the orifices 68. As best shown in FIG. 4, each drop detector 100 includes a light emitter 102 operable to emit a beam of light 104 through a respective mixing chamber 22 and a light sensor 106 positioned opposite the light emitter 102 to detect the light beam 104. Each light emitter 102 is connected to the circuit board 80 via a conductor 103. The light beam 104 intersects the ejection path of drops 108 dispensed from orifice 68 such that when a fluid drop 108 travels through the light beam 104, the light sensor 106 sends a signal to the controller 30 indicating the presence of the drop 108. If the drop detector does not detect that a drop has been ejected from the orifice 68, the controller 30 activates an alarm, or other warning device, to warn the subject and/or health care professional monitoring the subject. The alarm can be an audio alarm operable to provide an audible signal, such as a beeping sound or a buzzer, and/or a visual alarm, such as one or more indicator lights mounted in a convenient position on the dispensing apparatus 12. The alarm also may take the form of a written warning displayed on the display screen 38. Alternatively, the alarm can provide a tactile signal, such as a vibratory or vibrating signal similar to those used on pager devices.

In another implementation, the controller 30 calculates the actual frequency at which drops are being ejected from each orifice 68 based on signals from the drop detectors 100 and compares the actual frequency to the pre-set firing frequency of each orifice 68 to ensure that the prescribed dosage is being administered to the subject at the proper rate. If a jet dispenser is dispensing fluid faster or slower than the required rate, then the controller 30 activates the alarm, displays a warning on the display screen 38, and/or controls the jet dispenser to immediately stop dispensing fluid.

Drop detectors other than the illustrated optical drop detectors also can be implemented in the dispensing apparatus. For example, piezoelectric elements can be mounted to the inside surfaces of mixing chambers 22 to detect drops impinging the piezoelectric elements or the fluid in the mixing chambers, such as disclosed in U.S. Pat. No. 4,583,975 discussed above. In another example, an electrostatic drop detector may be used to detect the firing frequency as well as the volume of drops that are ejected from the jet dispensers. The controller 30 then calculates the dispensing rate of each jet dispenser and initiates a particular protocol (e.g., activating an alarm and/or stopping a jet dispenser from ejecting drops) if the dispensing rate is greater or less than the required rate.

In another application of the dispensing apparatus 12, one or more bioactive compositions can be dosed into the fluid manifold 18 and then administered to a subject without being diluted in an infusion liquid. Of course, in such an application, the fluid manifold 18 would not require fluid inlets 86 for receiving the infusion liquids.

Figures 6, 7:
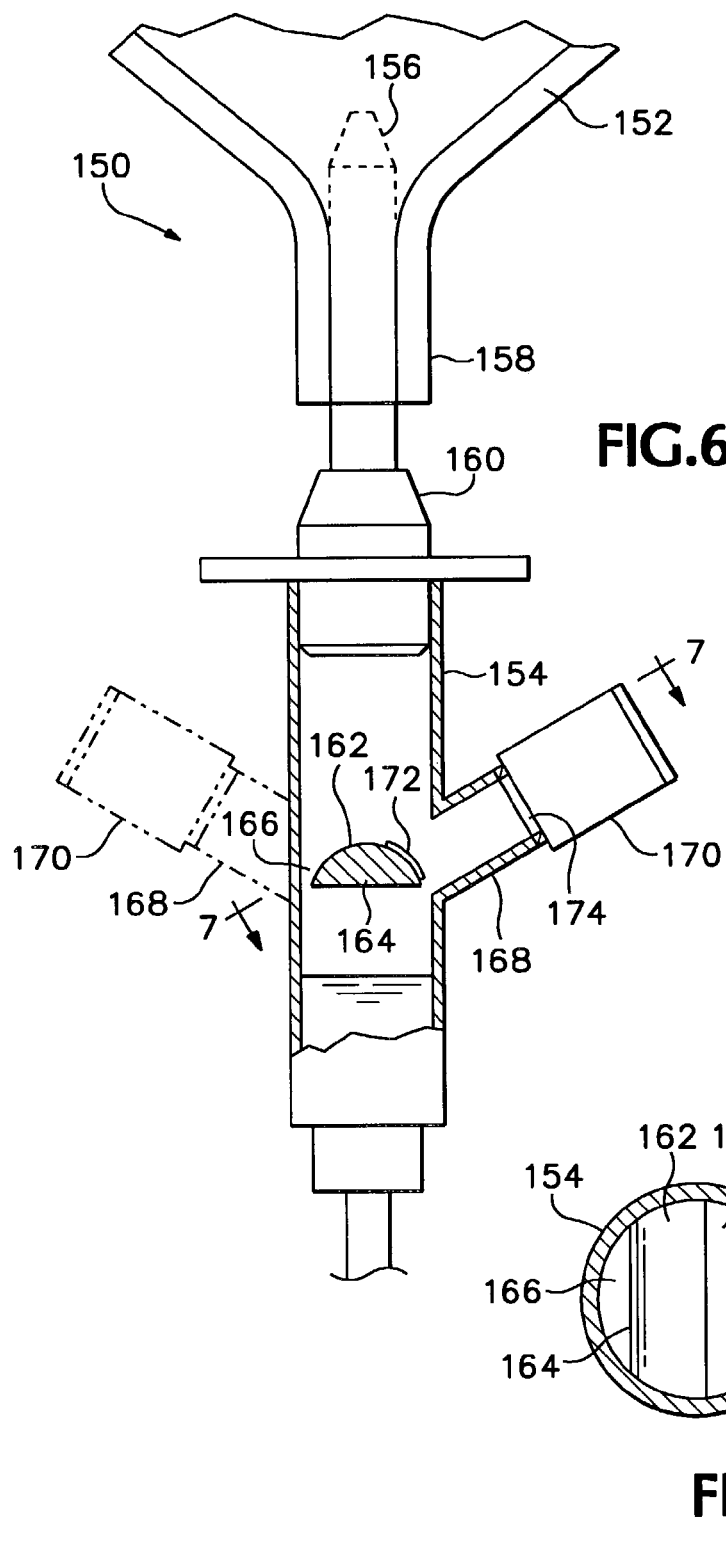
FIG. 6 is an elevational view of another embodiment of an infusion system, having a dispensing apparatus and a drip chamber, with the drip chamber shown partially in section.
FIG. 7 is an enlarged view of the drip chamber and dispensing apparatus of FIG. 7 taken along line 7-7 of FIG. 6.
Figure 8:
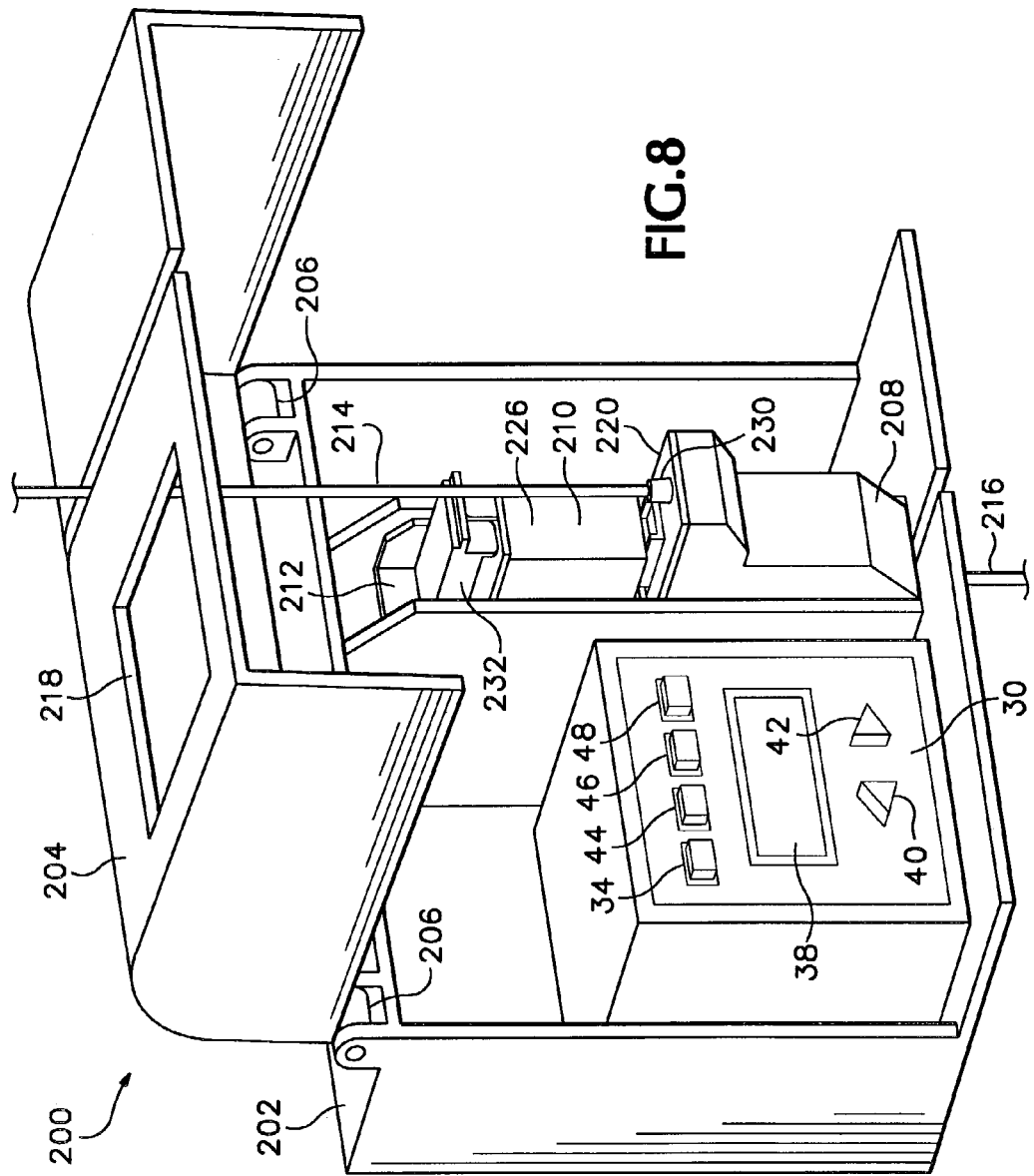
FIG. 8 is a perspective view of another embodiment of an infusion system.
Figure 9:
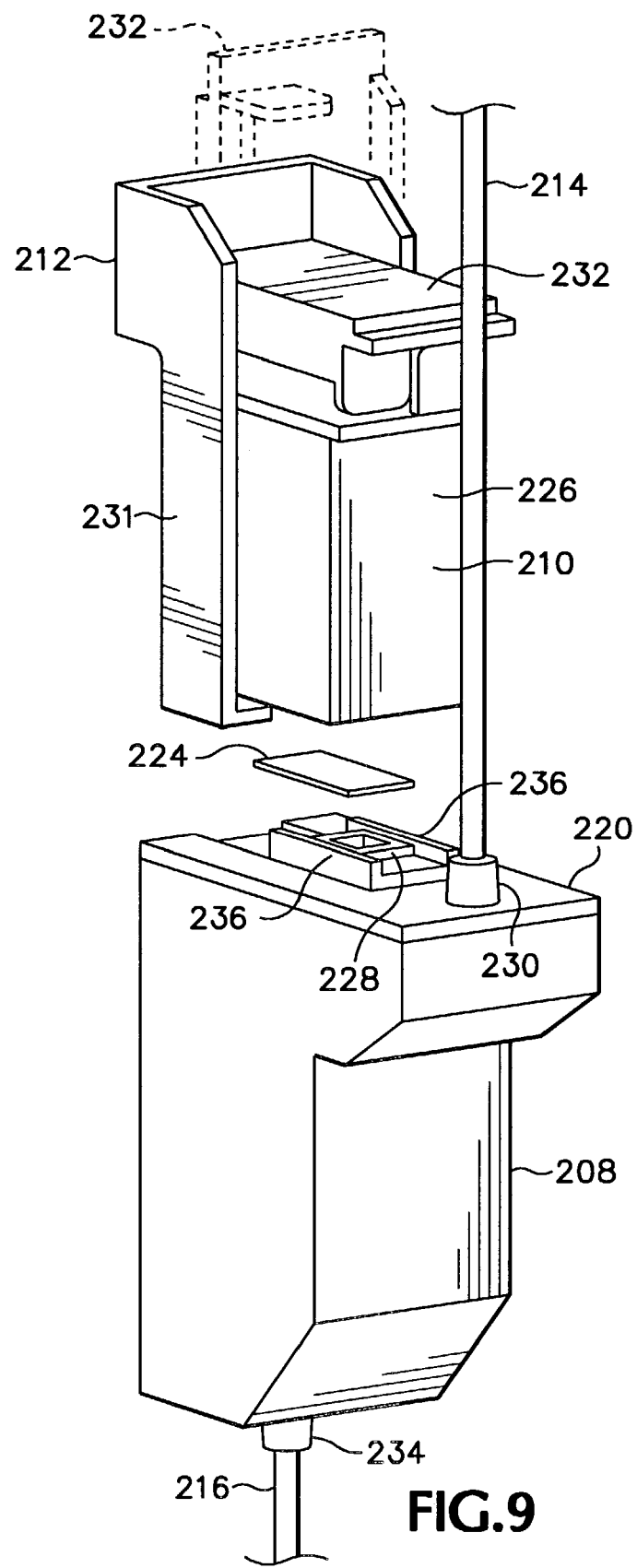
FIG. 9 is a perspective, exploded view of the dispenser, dispenser holder, and fluid manifold of the system of FIG. 8.

FIGS. 6 and 7 illustrate another infusion system, indicated generally at 150, for administering a bioactive composition to a subject. The illustrated system 150 includes a fluid container 152 for containing an infusion liquid and a drip chamber 154 (which serves as the fluid manifold in this embodiment) for receiving the infusion liquid. The drip chamber 154 may include an upwardly extending spike 156 used to puncture the outlet portion 158 of the fluid container 152, as generally known in the art. The spike 156 has an internal passageway that directs fluid from the container 152 to flow into a drop former 160 configured to produce drops of fluid that fall into the drip chamber 154. The construction of drop former 160 can be conventional. In particular embodiments, for example, the drop former includes a narrow fluid conduit (not shown) that produces drops due to the surface tension of the fluid flowing through the conduit. The drop former 160 can be integral with the spike 156 as shown in FIG. 6, or alternatively, the drop former and the spike can be separately formed, interconnecting components.

The drip chamber 154 desirably includes a drip surface 162 positioned underneath the outlet of the drop former 160 such that drops of the infusion liquid fall from the drop former onto the drip surface 162 before accumulating in the bottom portion of the drip chamber 154. The illustrated drip surface 162 is the convex upper surface of a rib 164 extending radially across the inside of the drip chamber 154. Openings 166 are defined between the sides of rib 164 and the inside surface of the drip chamber 154 to allow fluid to flow off of the drip surface 162 and accumulate at the bottom of the drip chamber 154.

The drip chamber 154 also includes a fluid inlet conduit 168. Mounted to the end of the inlet conduit 168 is a dispensing apparatus 170 for dosing one or more bioactive compositions into the drip chamber 154. The drip chamber 154 can include an additional inlet conduit 168, with an additional dispensing apparatus 170, as shown in phantom in FIG. 6. The construction of dispensing apparatus 170 is similar to the construction of the dispensing apparatus 12 shown in FIGS. 2-4. One difference between apparatus 12 of FIGS. 2-4 and apparatus 170 of FIGS. 6 and 7 is that the latter does not include a fluid manifold 18. In lieu of fluid manifold 18, droplets of bioactive composition are dispensed from one or more fluid reservoirs of dispensing apparatus 170 into the drip chamber 154 for mixing with the infusion liquid. A gasket 174 can be interposed between the opening of the fluid conduit and apparatus 170 to provide a fluid-tight seal therebetween. As in the previous embodiments disclosed herein, a controller (e.g., a controller 30) can be used to control the operation of the apparatus 170. The controller can be mounted to the apparatus or remotely mounted and connected via a link 176 (FIG. 7).

The system 150 also may include a drop detector for detecting the presence of drops ejected from the dispensing apparatus 170 and/or for detecting various other characteristics of the drops that are ejected from the dispensing apparatus 170. In the illustrated embodiment, a piezoelectric element 172 of a piezoelectric detector can be mounted on the drip surface 162 for detecting drops dispensed from the dispensing apparatus 170. In other embodiments, an electrostatic drop detector, or an optical drop detector, such as a drop detector 100 (FIGS. 3 and 4), can be used.

As shown in FIG. 6, the dispensing apparatus 170 desirably is positioned such that ejected drops impinge the piezoelectric element 172, or alternatively, the drip surface 162 itself if the piezoelectric element 172 is not provided. This allows the infusion liquid to mix with the bioactive composition as it flows over the drip surface 162 to facilitate dispersion of the bioactive composition in the infusion liquid.

FIGS. 8 and 9 illustrate another infusion system, indicated generally at 200, for administering a bioactive composition to a subject. As shown in FIG. 8, the illustrated system 200 includes a main housing 202 and a door 204 mounted at hinges 206. The door 204 is swingable between a closed position and an open position (as shown in FIG. 8) to access the components inside the housing 202. Mounted inside the housing 202 is a controller 30, a fluid manifold 208, a dispenser 210 for dispensing droplets of bioactive composition into the fluid manifold 208, and a dispenser support 212. The door 204 can include an opening 218 to allow a user to access the controller 30 without opening the door 204. A fluid conduit 214 delivers an infusion liquid from a fluid container (not shown in FIGS. 8 and 9) to the fluid manifold 208. An outlet fluid conduit 216 delivers a solution of the infusion liquid and a bioactive composition to a subject or to a pump for pumping the solution into the subject.

As shown in FIG. 9, the fluid manifold 208 in the illustrated configuration includes a cover, or lid, 220 that also serves as an interface between the fluid manifold 208 and the dispenser 210. The cover 220 is formed with a first fluid inlet (not shown) positioned between ribs 236 and dimensioned to receive drops of fluid ejected from the dispenser 210. The cover 220 also is formed with a second fluid inlet 230 for receiving the infusion liquid from fluid conduit 214 and a fluid outlet 234 for discharging solution to the outlet fluid conduit 216.

In the illustrated embodiment, the dispenser 210 includes a reservoir portion 226 for containing fluid and a thermal inkjet substrate 224 formed with a plurality of ejection orifices (not shown) and corresponding heater elements (not shown) (e.g., resistors). When assembled, the substrate 224 is positioned between the ribs 236 to align the orifices over the first fluid inlet in the cover 220. A gasket, or seal, 228 desirably surrounds the first fluid inlet to provide a fluid-tight seal between the fluid manifold 208 and the dispenser 210.

The illustrated dispenser support 212 includes a main body 231 and latch 232 hingedly connected to the main body 231 for releasably securing the dispenser 210. The latch 232 is pivotable between a latched position (as shown in FIG. 9) engaging the dispenser 210 and an unlatched position (as shown in phantom in FIG. 9) to allow removal and replacement of the dispenser 210.

In the particular embodiments, the dispenser 210 is a conventional inkjet cartridge (also known as a pen), and the dispenser support 212 is a conventional printer carriage configured to receive the cartridge. The construction of dispenser 210 can be modified from a conventional inkjet construction to accommodate, for example, the characteristics of the particular fluid to be dispensed. The cartridge can be a single-chamber cartridge, or alternatively, a multi-chamber cartridge that can be used to dispense more than one type of bioactive composition. In addition, the cartridge can have an "on-axis" configuration or an "off-axis" configuration, as discussed above. For example, the dispenser 210 and support 212 can be any of various commercially available thermal or piezoelectric cartridges and carriages, such as any of the 500, 700, 800, and 900 series TIJ (thermal inkjet) carriage and pen assemblies, available from Hewlett-Packard Company for use in inkjet printers.

Many other variations of devices and methods are within the scope of this disclosure. For example, an optical sensor can be incorporated into the controller 30 to read patient identification, such as a bar code on a patient's hospital identification bracelet, with this information being used by the controller to adjust the dosage and/or type of medication administered.

This specification has described several detailed examples, which are not intended to be limiting. Rather, these examples are provided to illustrate some of the embodiments which come within the scope of the following claims.

We claim:

1. An apparatus for administering a bioactive composition to a subject, comprising:

a plurality of inkjet dispensers, each inkjet dispenser being operable to dispense discrete quantities of droplets of the bioactive composition;

a mixing unit having a plurality of mixing chambers, each mixing chamber being configured to receive the bioactive composition dispensed from a respective inkjet dispenser, each mixing chamber having an inlet for receiving an infusion liquid to be mixed with the bioactive composition and an outlet for discharging a mixture of the infusion liquid and the bioactive composition; and a plurality of fluid reservoirs for containing the bioactive composition, each fluid reservoir being fluidly connected to a respective inkjet dispenser;

wherein each inkjet dispenser comprises an ejection orifice, the ejection orifices being formed in a die interposed between the fluid reservoirs and the mixing chambers, each ejection orifice being fluidly connected to a respective fluid reservoir and operable to eject a controlled amount of the bioactive composition into a respective mixing chamber.

2. The apparatus of claim 1, wherein the inkjet dispensers are piezoelectric droplet jet dispensers.

3. The apparatus of claim 1, wherein the inkjet dispensers are thermal droplet jet dispensers.

4. The apparatus of claim 1, wherein each inkjet dispenser further comprises a heating element to heat a quantity of the bioactive composition, thereby causing a droplet of the bioactive composition to be ejected from a respective ejection orifice.

5. The apparatus of claim 1, further comprising a drop detector operable to detect a characteristic of the droplets of the bioactive composition that are dispensed from at least one of said inkjet dispensers.

6. The apparatus of claim 5, wherein the drop detector is operable to detect a presence of droplets dispensed from at least one of said inkjet dispensers.

7. The apparatus of claim 5, wherein the drop detector is operable to detect a rate at which the droplets are ejected from at least one of said inkjet dispensers.

8. The apparatus of claim 5, wherein the drop detector is operable to detect a volume of the droplets dispensed from at least one of said inkjet dispensers.

9. The apparatus of claim 5, further comprising an alarm operatively connected to the drop detector and operable to provide a warning if the characteristic detected by the drop detector does not satisfy a predetermined condition.

10. The apparatus of claim 9, wherein the alarm provides a warning if the drop detector does not detect a presence of droplets.

11. The apparatus of claim 5, wherein the drop detector comprises a plurality of the drop detectors for detecting a characteristic of the droplets dispensed from each inkjet dispenser.

12. The apparatus of claim 5, wherein the drop detector comprises an optical drop detector including a light source producing a light beam and a light sensor positioned to detect the light beam, the light beam intersecting an ejection path of the droplets ejected from at least one of said inkjet dispensers.

13. The apparatus of claim 1, further comprising a controller for actuating the inkjet dispensers.

14. The apparatus of claim 13, wherein the controller is operable to control the inkjet dispensers to dispense the bioactive composition from each inkjet dispenser at a different dispensing rate.

15. The apparatus of claim 1, further comprising:

a drop detector for detecting a characteristic of a droplet dispensed from one of said inkjet dispensers and providing a signal corresponding to the detected characteristic; and a controller operable to receive said signal from the drop detector and to stop the inkjet dispenser from dispensing the bioactive composition if the detected characteristic does not satisfy a predetermined condition.

16. The apparatus of claim 1, wherein the inkjet dispensers comprise a first inkjet dispenser and a second inkjet dispenser, the first inkjet dispenser operable to dispense droplets of a predetermined size, the second inkjet dispenser operable to dispense droplets of a predetermined size different than the size of droplets dispensed from the first inkjet dispenser.

17. The apparatus of claim 1, wherein each mixing chamber has a drip surface and each inkjet dispenser is configured to dispense droplets of the bioactive composition onto a respective drip surface.

18. The apparatus of claim 17, wherein the inlet of each mixing chamber is configured to direct the infusion liquid to flow over a respective drip surface.

19. The apparatus of claim 1, further comprising a plurality of fluid conduits fluidly connected to the outlets of the mixing chambers for delivering mixtures of the infusion liquid and the bioactive composition to the subject.

20. The apparatus of claim 1, further comprising a plurality of pumping chambers for receiving mixtures of the infusion liquid and the bioactive composition from the mixing chambers and pumping said mixtures into the subject.

* * * * *